US006429936B1

United States Patent
Scaduto (10) Patent No.: US 6,429,936 B1
(45) Date of Patent: Aug. 6, 2002

(54) SYNCHRONOUS MULTIWAVELENGTH FLUORESCENCE SYSTEM

(75) Inventor: Russell Scaduto, Hummelstown, PA (US)

(73) Assignee: C&L Instruments, Hummelstown, PA (US)

( * ) Notice: Subject to any disclaimer, the term of this patent is extended or adjusted under 35 U.S.C. 154(b) by 0 days.

(21) Appl. No.: 09/369,526

(22) Filed: Aug. 6, 1999

Related U.S. Application Data (60) Provisional application No. 60/107,362, filed on Nov. 6, 1998.

(51) Int. Cl.$^7$ ............................................. G01N 21/64
(52) U.S. Cl. ..................... 356/417; 356/418; 250/458.1
(58) Field of Search ................................. 356/417, 418; 250/458.1, 459.1, 461.1, 461.2

(56) References Cited

U.S. PATENT DOCUMENTS

| | | | |
|---|---|---|---|
| 4,477,190 A | * | 10/1984 | Liston et al. ................ 356/418 |
| 4,817,020 A | * | 3/1989 | Chande et al. .......... 250/339.04 |
| 5,159,410 A | | 10/1992 | Pollak et al. ................ 356/417 |
| 5,194,913 A | | 3/1993 | Myrick et al. ............... 356/301 |
| 5,233,197 A | | 8/1993 | Bowman et al. .......... 250/461.1 |
| 5,422,730 A | | 6/1995 | Barlow et al. ............... 356/417 |
| 5,436,718 A | | 7/1995 | Fernandes et al. ............. 356/73 |

* cited by examiner

Primary Examiner—F. L Evans
(74) Attorney, Agent, or Firm—Carmen Santa Maria; McNees Wallace & Nurick LLC (57) ABSTRACT

A multichannel system for synchronizing independently driven filter wheels. The system is comprised of a means for controlling operation of the system by providing appropriate instructions. A clock provides timing signals to assure that instructions are executed at the correct time. A device having a programmable memory with the ability to receive and transmit signals is in communication with the clock and the control means. This programmable memory device, in response to a signal from the control means executes a preselected program and transmits a signal in response to an instruction receive from the control means. Two assemblies, each comprised of a programmable motor controller, a motor driver and a motor are attached to an encoder and a filter wheel having a plurality of filters. The assemblies are connected to a power source. In response to the signal from the programmable memory device, each controller executes a preselected program that permits the controller to resolve the position of the encoder and hence the filter wheel with respect to an indexing means on the encoder at any instant in time. Thus the positions of the filter wheels can be synchronized with one another at any instant of time. In this manner, incident light of a single wavelength filtered by a first filter wheel and incident on a sample in a sample holder, for instance in a fluorescent microscope, can be synchronized with light emitted by the sample and filtered by a second filter wheel. The filtered, emitted light of a single wavelength provides characteristic information about activity within the sample.

21 Claims, 5 Drawing Sheets

SYNCHRONOUS MULTIWAVELENGTH FLUORESCENCE SYSTEM

CROSS-REFERENCE TO RELATED APPLICATION

This application claims benefit of U.S. Provisional Application No. 60/107,362, filed Nov. 6, 1998.

BACKGROUND OF THE INVENTION

1. Field of the Invention

This invention relates generally to the field of optical illumination and detection of biological activity in cells, organs or other samples, and more specifically to a method and apparatus for observing virtually instantaneously, the activity of a sample by illuminating the sample and measuring the light emitted from the sample.

2. Discussion of the Prior Art

Spectroscopy is the measurement and interpretation of electromagnetic radiation absorbed or emitted when the molecules or atoms of a sample move from one energy level to another. In biological research, an observation in the changes of the optical absorption and emission of light provide valuable scientific information of what is occurring in the cell, organ or sample, for example, the progress of an ongoing chemical reaction.

Chemical analysis using absorption spectroscopy allows for the determination of concentrations of specific components, to assay reactions and to identify individual compounds while fluorescence is a physical phenomena based upon the ability of some substances to absorb and subsequently emit radiation. The emitted radiation generally has a lower energy level and a longer wavelength than the absorbed radiation which is used to excite the sample. Furthermore, the absorption of the incident light is wavelength dependent. Thus, a sample will only fluoresce when the excitation wavelength of the incident light falls within the excitation band for the substance at that particular time. The phase relationship between variations in the excitation or incident light and the light emitted from the sample is very important in observing changes in a substance as an event or reaction occurs.

One of the deficiencies of the prior art has been the lack of ability to faithfully observe ongoing changes in a sample as a reaction occurs, when the reaction requires detection at several wavelengths of light. With the present state of the art, it is often required in analytical procedures that reactions or assays be monitored at more than one wavelength. For observation systems that can change wavelengths in a little as one second, or theoretically, in $1/30^{th}$ of a second, there is high likelihood that a change in a sample occurring in $1/100^{th}$ or $1/1000^{th}$ of a second will not be detected. Also, in some analytic procedures, it is a requirement to change the wavelength of the excitation and emission light to permit detection at several wavelengths in order for a meaningful measurement to be made.

In newer approaches in the detection of events that occur in cells or other biologically related specimens, meaningful data must be obtained from the compilation of measurements made at more than one excitation and/or emission wavelength. As such, the speed of detection by the detecting device (PMT) is as important as the ability of the instrument to change the excitation and/or detect emission wavelength in a rapid fashion in-between or during the detection events. An instrument that has the ability to rapidly change excitation wavelengths and to rapidly detect a plurality and emission wavelengths in a short period of time, and synchronize events based on detection of light emitted by the sample, can monitor events that occur in the specimen with higher fidelity. Examples of these approaches and procedures for detection are the use of readily available fluorescent chemicals that exhibit spectrum-shifting properties that are dependent on their environment. Fura-2 and indo-1 are two typical chemicals used for the determination of calcium concentration that exhibit spectrum-shifting properties in certain environments.

One device for excitation/emissions measurements invented by Barlow et al. and described in U.S. Pat. No. 5,422,730, sets forth a system which permits for detection by a CCD camera of ongoing reactions in a particular sample. The device set forth below by Barlow et al. uses a pair of filter wheels to select a plurality of filters that transmit pre-selected light wavelengths, but the selection of wavelengths by the two filter wheels are performed in a sequential fashion. The limitations of this device are that it permits detection of events at only one excitation and one emission wavelength. The sequential selection of wavelengths by the filter wheels detrimentally slows the response time of the instrument to obtain meaningful data if more than one excitation or more than one emission wavelength measurement is required for meaningful information.

Other devices for observing reactions in samples can excite a sample using two different wavelengths simultaneously or can measure two different wavelengths at the same time by utilizing beam splitting devices. Some of the more advanced equipment is capable of measuring four different wavelengths emitted by a sample by use of vibrating mirrors, choppers or dichroic mirrors. Each of these devices has the ability to select an excitation or emission wavelength in a rapid fashion, but they do comprise a system in which the excitation and emission wavelengths are changed simultaneously and are synchronized to the detection of light intensity.

There is lacking in the biological field a photometer that is capable of exciting a cell or sample with a plurality of wavelengths, typically more than four, and virtually instantaneous observing the ongoing reaction by analyzing a plurality of wavelengths, typically more than four, emitted by the cell, organ or sample, either in-vitro or in-vivo, that does not interfere with the activity of the cell, organ or sample, and which is inexpensive and easy to operate. While there are instruments available that can make measurements quickly, their ability to do so at multiple wavelengths is limited. Typically, these instruments utilize spinning or vibrating mirrors to change either the excitation or the emission wavelengths (but not both) quickly. Conversely, instruments capable of exciting samples and taking measurements at multiple wavelengths are slow. There is a need for an instrument that can accomplish both excitation and detection quickly.

SUMMARY OF THE INVENTION

Accordingly, an advantage of the present invention is the capability of exciting a cell, organ or sample with a plurality of wavelengths and measuring a plurality of wavelengths emitted by the cell, organ or sample. The measurements are performed hundreds of times per second and may be performed thousands of times per second so that rapidly occurring changes can be observed. Despite the rapid number of measurements made by the device of the present invention, the narrow wavelength band of incident light is always synchronized with a narrow wavelength of emitted light.

Another advantage of the present invention the equipment used for florescent illumination and detection is relatively inexpensive to manufacture and does not require a high degree of skill to use.

Newer analytical procedures require the measurement of light intensity at more than one excitation or emission wavelength in order to get meaningful data. Measurement at one wavelength is not meaningful in the absence of another related measurement at a different wavelength. The results of both measurements are required for a calculation in the assay procedure. An advantage of the present invention is that it provides the capability to rapidly excite an assay or sample at a number of preselected wavelengths and to measure the emission from the assay at a number of preselected wavelengths while correlating the excitation wavelengths to the emissions wavelengths.

Meaningful data from an assay requires the capability to detect and measure a plurality of wavelengths of light emitted from an assay in a very short time frame. An advantage of the present invention is that it has the capability to both excite a sample or assay and detect the emissions from an assay at a plurality of wavelengths in a very short time frame so that meaningful multi-wavelength measurements can be made and recorded.

Still another advantage of the present invention is that it can readily be adapted for use with an optical microscope for real time viewing, with a CCD camera for real time viewing and recording or with a computer for digitizing, analyzing and recording the output from the sample.

In its broadest embodiment, the present invention is a multichannel system, each channel being independent yet synchronized with the other channel. The multichannel system can be used effectively for high speed synchronization of light from a light source incident on a cell, tissue, organ or other biological sample and light emitted from the cell, tissue, organ or other biological sample as a result of biological or chemical activity occurring in it. The multichannel system is comprised of a means for controlling operation of the system by issuing instructions. This central control unit is typically a CPU or central processing unit that is capable of executing a program that includes a plurality of sets of instructions or programs. Each program or series of instructions sets forth the operations that are to be performed by the system so that the desired measurements can be made. The operator preselects the program that is to be used through the central control unit. The central control unit is a device having a programmable memory which may optionally be connected to another device having a programmable memory, such as a programmable logic device (PLD) that is in communication with the central control unit. The device has a programmable memory for receiving instructions from the central control unit to execute a pre-selected program that has been preprogrammed into the device. The device also receives instructions from other hardware, these additional instructions being required for execution of the preselected program. The multichannel system also includes at least two independent integrated circuit devices capable of being programmed, such as preprogrammed motor controllers, that receive instructions from the devices and information from other hardware. Instrumental in the synchronization of the system is a clock that provides a timing signal to initiate operation of the program in the device having a programmable memory, such as the PLD, which in turn provides additional signals to permit synchronization of the operations of the motor controllers. Upon receiving a signal from the central control unit, the programmable device initiates operation of the preselected program in its memory that includes transmitting a signal simultaneously to each of the controllers to initiate their preprogrammed series of instructions. Connected to each motor controller is a motor driver, which receives power from any conventional power source. The motor drivers operate in response to signals received from their respective motor controllers. The motor drivers drive motors to which they are connected, each motor having a motor shaft. Connected to each motor shaft, so that they rotate with the shaft, is an encoder and a filter wheel, each filter wheel including a plurality of filter positions for holding filters. Each controller is capable of resolving the position of the encoder, and hence the filter wheel with a high degree of accuracy as they rotate on the motor shaft. The ability of the controllers to resolve their position is based on the ability of encoders to produce a plurality of pulses, and their ability to index these pulses to an initial position. Because each encoder is connected to the common shaft of the motor, resolution of the encoder position simultaneously resolves the position of the motor shaft and the corresponding filter wheel. Each controller resolves the encoder position with respect to the initial index pulse provided to the individual controller by the encoder. Each controller, in executing its set of instructions, receives signals from its respective encoder showing the actual position of the encoder with respect to its initial pulse and compares this actual position to a calculated position. If the actual and calculated positions do not correspond, the controller sends additional signals to the motor driver to speed up or slow down the motor so that the encoder position can be changed in the appropriate fashion. In this way the calculated position and the actual position of the encoder are brought into correspondence. Of course, because the encoder and the filter wheel are rotating on the same shaft, the position of the filter wheel is also known.

The programmable device first synchronizes the initial position of the filter wheels and encoders by providing a signal that sets them to the same stationary index position. In response to a command from the central control unit, the programmable device issues an instruction to each of the motor controllers to initiate spinning of the motors at the same constant speed at the same time based on the clock, using a preprogrammed sequence in each controller. The programmable device may optionally issue the instruction simultaneously to the controllers to initiate the program immediately. The controllers respond and enter a program loop in which they determine the actual position of the encoders at a given time and compare these actual positions to calculated positions of the encoders, the calculated positions being a function of motor speed and time. If the actual position is lagging the calculated position, the controller sends a signal to the motor driver to increase the speed of the motor, or if ahead of the calculated position, to decrease the speed of motor. Since both controllers are operated from the same clock, and are instructed to initiate operation simultaneously at the same speed, they both will calculate the same calculated position for their respective encoders in each cycle of their program loops. Adjustments by the controllers to the actual positions of their respective encoders will be based on the deviation of the encoders from their calculated positions. Because the calculated position of each encoder is the same, based on simultaneous execution of the same program within the programmable memory of the encoder, the controllers synchronize the positions of the encoders. These adjustments to the respective encoders are performed independently by each controller. This allows the two controllers to operate independently, while keeping the two encoders in synchronization. Because the filter wheels are fixed in relation to the encoders, operation of the filter wheels is also synchronized.

The synchronous yet independent operation of the filter wheels in this multichannel system provides the advancement in the state of the art. Since each filter wheel includes a plurality of filters, each of which transmit a narrow band of wavelengths, synchronization of a filter wheel having preselected filters to transmit a first narrow band of light of first preselected wavelengths to excite a sample, with a second filter wheel having preselected filters to receive a second narrow band of light of second preselected wavelengths permits rapid observations and measurement of emissions from the same sample when the emissions correspond to changes in the sample as a result of biological or chemical activity.

Other features and advantages of the present invention will be apparent from the following more detailed description of the preferred embodiment, taken in conjunction with the accompanying drawings which illustrate, by way of example, the principles of the invention.

DETAILED DESCRIPTION OF THE PREFERRED EMBODIMENT

The apparatus and methods of the present invention are utilized to excite a biological sample with known preselected wavelengths of light and to observe and measure the intensity of emitted wavelengths of light from a biological sample or assay. The emitted light at multiple wavelengths provides information of ongoing chemical or biological activity occurring in the sample. The sample may be a cell, an organ or an organism, and the observations may be made in vitro or in vivo. Because the biological or chemical activity can and does occur very rapidly, in the order of hundredths or even thousands of a second, the present invention permits the biological sample to be irradiated with light from a single wavelength or from a plurality of wavelengths, and for a plurality of observations or measurements to be made either at a single wavelength or at a plurality of wavelengths in fractions of a second. As used herein, the term single wavelength refers to the narrow band of light transmitted through a single filter on a filter wheel, since the narrow band of transmitted wavelengths is closely centered about a preselected wavelength. As used herein, the term plurality of wavelengths refers a plurality of the narrow bands of light transmitted through a plurality of filters on a filter wheel, each filter transmitting essentially a single wavelength of light. The incident light, which typically is a broad band spectrum of light, travels through a plurality of filters on a filter wheel in the excitation assembly of the system, while the emitted light travels through a series of filter wheels in the emission assembly of the system, the excitation assembly and emission assembly being independent, yet running in perfect synchronization.

Figure 1:
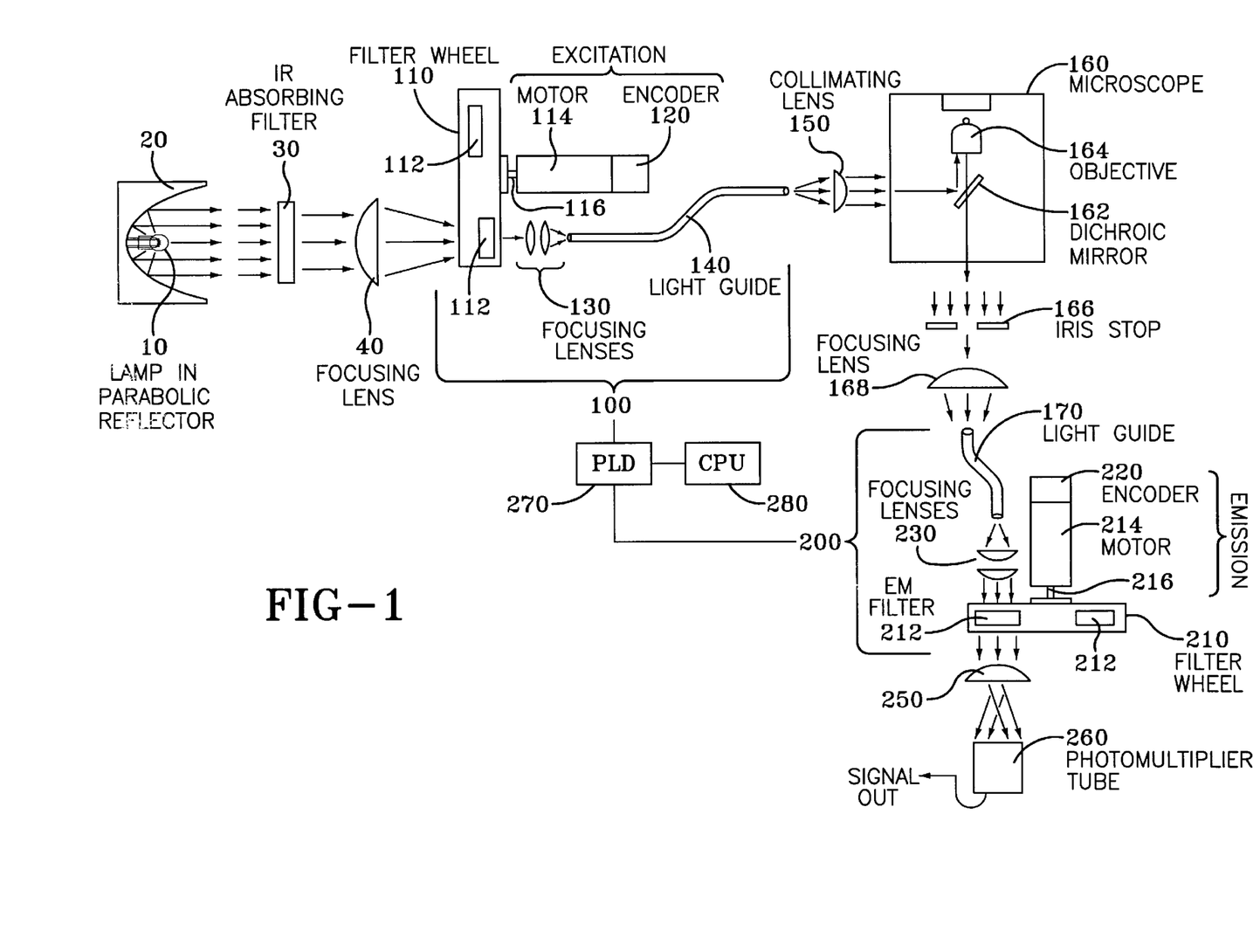
FIG. 1 is a schematic of a preferred embodiment of the present invention in a fluorescent microscope using a photomultiplier tube to capture light from the emission assembly.

Referring to FIG. 1, a broadband spectrum of light is produced by a light source, such as a xenon arc lamp 10. However, any source of light that produces a broad band spectrum of light may be used. Common available incandescent sources include tungsten and halogen lamps, while additional vapor sources include mercury, argon and mercury-xenon. An optional parabolic reflector 20 collimates the fluorescent light. The collimated light passes through an IR absorbing filter 30, where light (and corresponding heat) from the infrared spectrum is filtered, and then through a focusing lens 40 where it enters the excitation assembly 100 of the fluorescent microscope of the present invention. At this point the light is still comprised of a broad band spectrum of wavelengths, with only wavelengths corresponding to the infrared spectrum having been removed by filter 30. The light travels through one of a plurality of band pass filters 112 of 200 to 1000 nanometer (nm) center wavelength on a filter wheel 110. Each filter 112 is designed to permit the passage of a narrow band of wavelengths of light. In a preferred embodiment, the filter wheel includes eight filters. However, the number of filters may be increased or decreased, as may be the size of the filter wheel. A typical existing set-up has used a wheel having as few as four filters. Also, depending on the experiment, the filters 112 may transmit the same wavelengths, or as is more typical, different wavelengths. Any suitable filter may be used to filter the light, and many different filters are available depending on the nature of the experiment. The filters used in the preferred embodiment are interference filters, but neutral density filters and glass filters may also be used. A wide variety of filters of these types are available from Omega Optical, Inc. of Brattleboro, Vt. and Chroma Technology, Corp. of Brattleboro, Vt.

The filter wheel is attached to the shaft 116 of a motor 114 that rotates the filter wheel 110, in the preferred embodiment at a top regulated speed of 7500 rpm. Motor 114 is connected to a power supply (not shown). However, a larger motor could be used to drive the assembly at even high speeds, if necessary. Also attached to the shaft 116 of motor 114 is an encoder 120, which is used to establish the position of the filter wheel 110 at a time "t" in conjunction with a motor controller, a motor driver and a clock. The operation of the encoder 120 in conjunction with the motor controller 124 establish the position of filter wheel 110 and will be discussed in conjunction with a more detailed description of the excitation and emission assemblies below. Encoder 120 and motor 114 operate responsive to signals from a CPU and a programmable logic device (PLD). Encoder 120 provides feedback to controller 124 in the form of signals indicative of encoder position.

Each filter transmits only filtered light of a preselected wavelength. As the light is transmitted, passing through one of the preselected filters 112 of the rotating filter wheel 110, it is incident on a means for coupling the light to a fluorometer. The fluorometer in its broadest application is simply a sample chamber for holding the specimen to under examination. The fluorometer may be an instrument such as an optical microscope. In the best mode of practicing the invention, the light then passes through a focusing lens 130 and into a light guide 140, where it is delivered to a collimating lens 150. In the preferred embodiment, light guide 140 is quartz. However, other light guides such as optical fiber bundles and single optical fibers are also suitable for this function. In the preferred embodiment, after passing through collimating lens 150, the light illuminates the sample under observation in the fluorometer. In the preferred embodiment, the sample is mounted in a fluorescent microscope 160. There are many available fluorescent microscopes that may be used in this invention. One fluorescent microscope, used in the best mode for practicing the present invention, is the Olympus Model IX 70, available from the Olympus America, Inc. However, it will be understood that the sample could be mounted in a chamber in which it could be observed by a CCD camera (not shown), where light emissions from the sample are recorded by a suitable attached device. Alternatively, the chamber may contain instrumentation to detect light emissions as readings from the sample, and the readings can be transmitted to a computer for recordation and analysis. In yet another embodiment, the sample may be mounted in a standard optical microscope for observation, while recording of the light emissions could be done by standard photographic equipment. There are a variety of means for mounting a sample or specimen, while illuminating it and detecting the emissions from it that are compatible for use in the present invention.

In the preferred embodiment, the filtered light passes into the fluorescent microscope 160 and is reflected by a dichroic mirror 162 through an objective 164 and onto the sample. The sample may exist in vitro or in vivo. Further, fluorescent dyes may be added to the sample to further enhance the detection capabilities of the present invention. The use of these dyes is preferred, although not necessary, since they can either provide improved resolution abilities, the emitted light from the sample being usually very weak, or allow for observation of other modes, such as environmental conditions. The incident light raises the energy levels of the atoms and molecules of the sample. Depending on the biological or chemical activities occurring within the sample, as the sample decays, it will emit light of characteristic wavelength, which will have a lower energy and longer wavelengths than the excitation wavelength, dependent also upon the process. The wavelength of emitted light provides characteristic information about the on-going biological or chemical activities occurring within the sample. However, incident or excitation light of different wavelengths generally causes different emissions spectrum in a sample, again depending upon the activity of the sample at a point in time. In order to assess the activities occurring in a sample, it is important to both detect this emitted light and changes in the emitted light over a very short time. Because generally more than one activity occurs simultaneously, different wavelengths may be emitted at the same time. The plurality of filters enables the detection and separation of the different wavelengths. However, because the activity only may occur for a short time, the detection and separation must also be done rapidly.

As the emitted light is given off by the sample, some of it is gathered by the objective 164, which transmits it through dichroic mirror 162, through an optional variable iris stop 166 and into focusing lens 168. The iris stop provides the capability to limit the detection of emitted light from a preselected portion of the sample, if desired. The focusing lens 168 focuses the light into a light guide 170, which sends the emitted light, which may include a variety of wavelengths, into the emission assembly 200. The emission assembly 200 is virtually identical to the excitation assembly 100. The emitted light first passes through one of a plurality of band pass filters 212 on a rotating filter wheel 210. Each filter 212 is designed to permit passage of a single wavelength of light. In the preferred embodiment, the emission filter wheel has the same number of filters, eight, as the excitation filter wheel, so there is a one-to-one correspondence between the filters of the two wheels. However, this need not be the case. The filters may be arranged in any convenient manner, for example, the emission wheel 210 may contain four filters so that there is two to one correspondence between the excitation and emission filter wheels. Alternatively, the emission wheel 210 may contain 16 filters, so that there is one to two correspondence between the excitation and emission filter wheel. Furthermore, the filters in the filter wheel may each be selected so as to pass the same wavelength of light, or each may be selected so as to pass different wavelengths of light or any combination thereof. For example, if eight different excitation wavelengths are used to excite a sample, but, because of the reaction under study, it is only necessary to detect and observe the results from two characteristic wavelengths indicative of characteristic reactions of interest, then four filters corresponding to each of the two wavelengths would be inserted into the alternating filter positions in the eight filter positions on filter wheel 210. The large number of combinations available provides substantial flexibility to the present invention and should be apparent to those skilled in the art.

Figure 6:
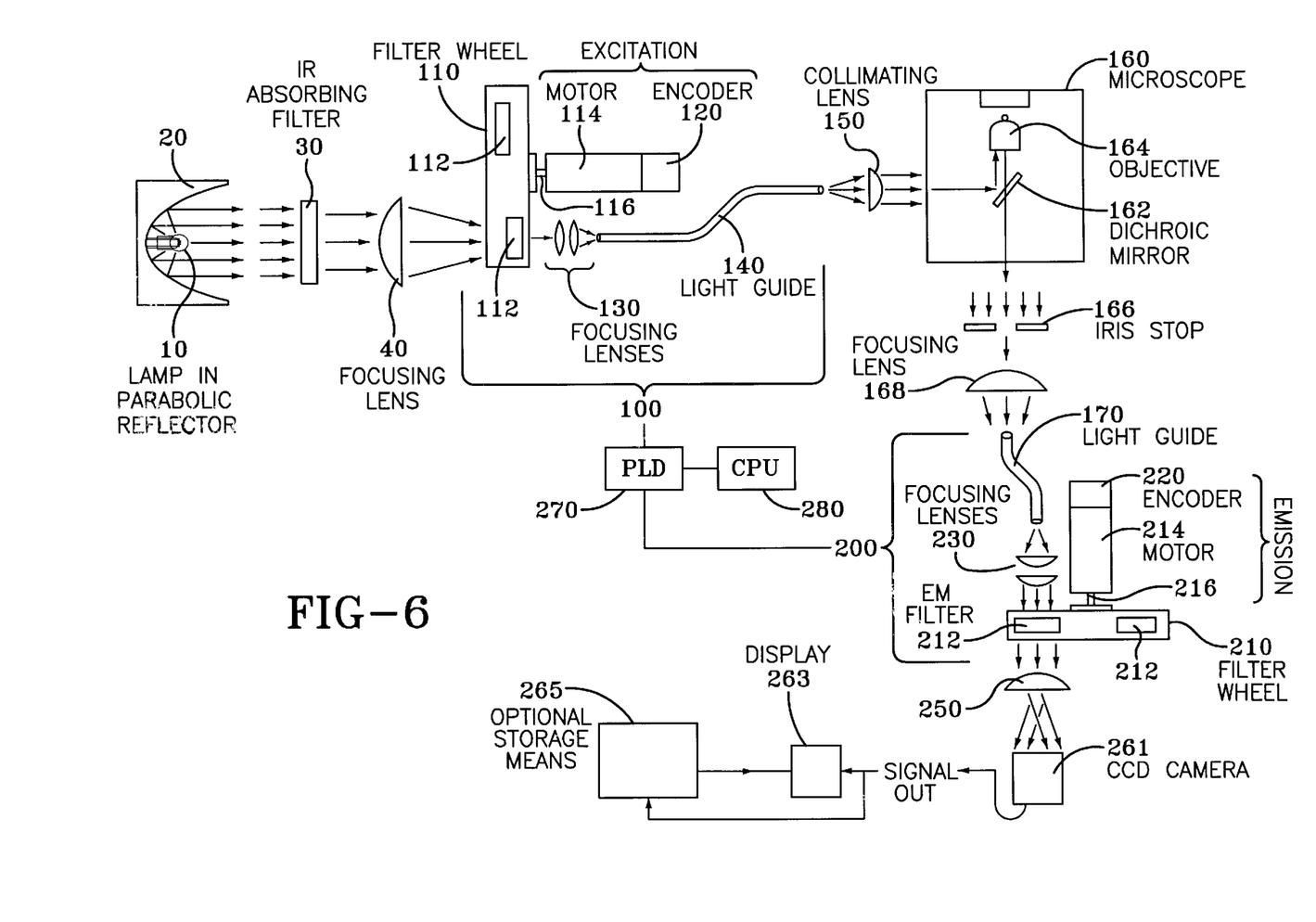
FIG. 6 is a schematic of a preferred embodiment of the present invention in a fluorescent microscope using a CCD camera to capture light from the emission assembly and a display to view images from the CCD camera, with an optional storage means to store images.

After the emitted light passes through a filter 212 on wheel 210, it then passes through a focusing lens 250 and to a photomultiplier tube where it is amplified. The resulting signal can then be sent to a signal conditioning device and then to a unit for storage or analysis, such as central processing unit 280 of the preferred embodiment. The emitted light may also be viewed by appropriate optical viewing equipment. Of course, a CCD camera 261, as shown in FIG. 6, provides a convenient method of viewing output from the emission assembly 200 and storing the output on an optional storage means 265 for archival purposes or simply for later viewing oil a display 263.

Because of the rapid speed at which reactions take place in a sample, whether the sample is a cell, organ or organism, for the apparatus to be effective, the sample must be excited by various wavelengths of light at speeds approaching or surpassing the speed of the reaction. Furthermore, the apparatus must also to be able to detect, resolve and observe the light emitted by the sample as it undergoes the biological or chemical changes at speed approaching or surpassing the speed of the reaction. However, the excitation events must be synchronized with the emissions events for the data to be meaningful. The apparatus of the present invention accomplishes this through a novel arrangement of independently and rapidly operated excitation assemblies and emission assemblies that are fully synchronized.

Figure 2:
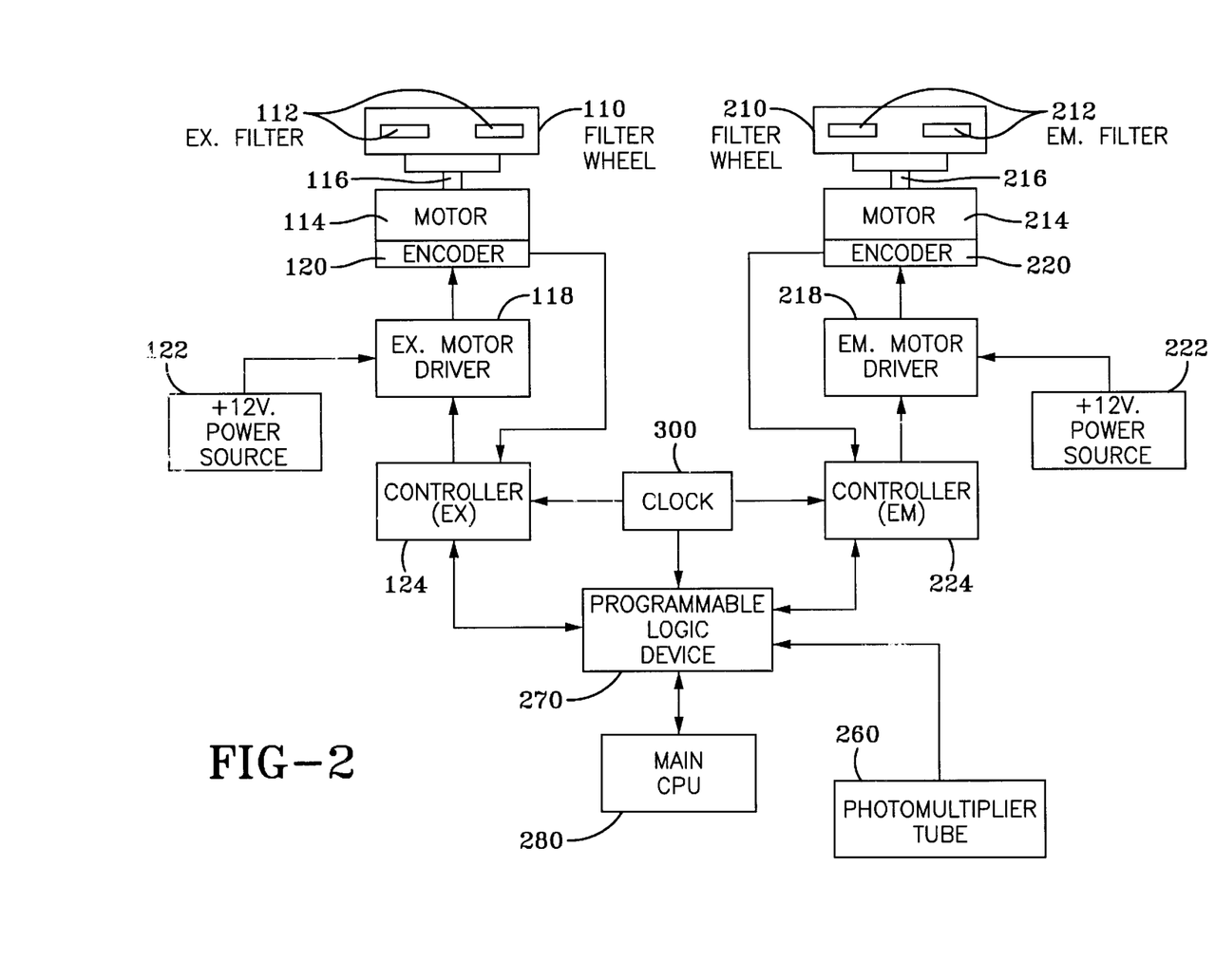
FIG. 2 is a schematic of the excitation and emission assemblies of the present invention in the fluorescent microscope application of FIG. 1.
Figure 3:
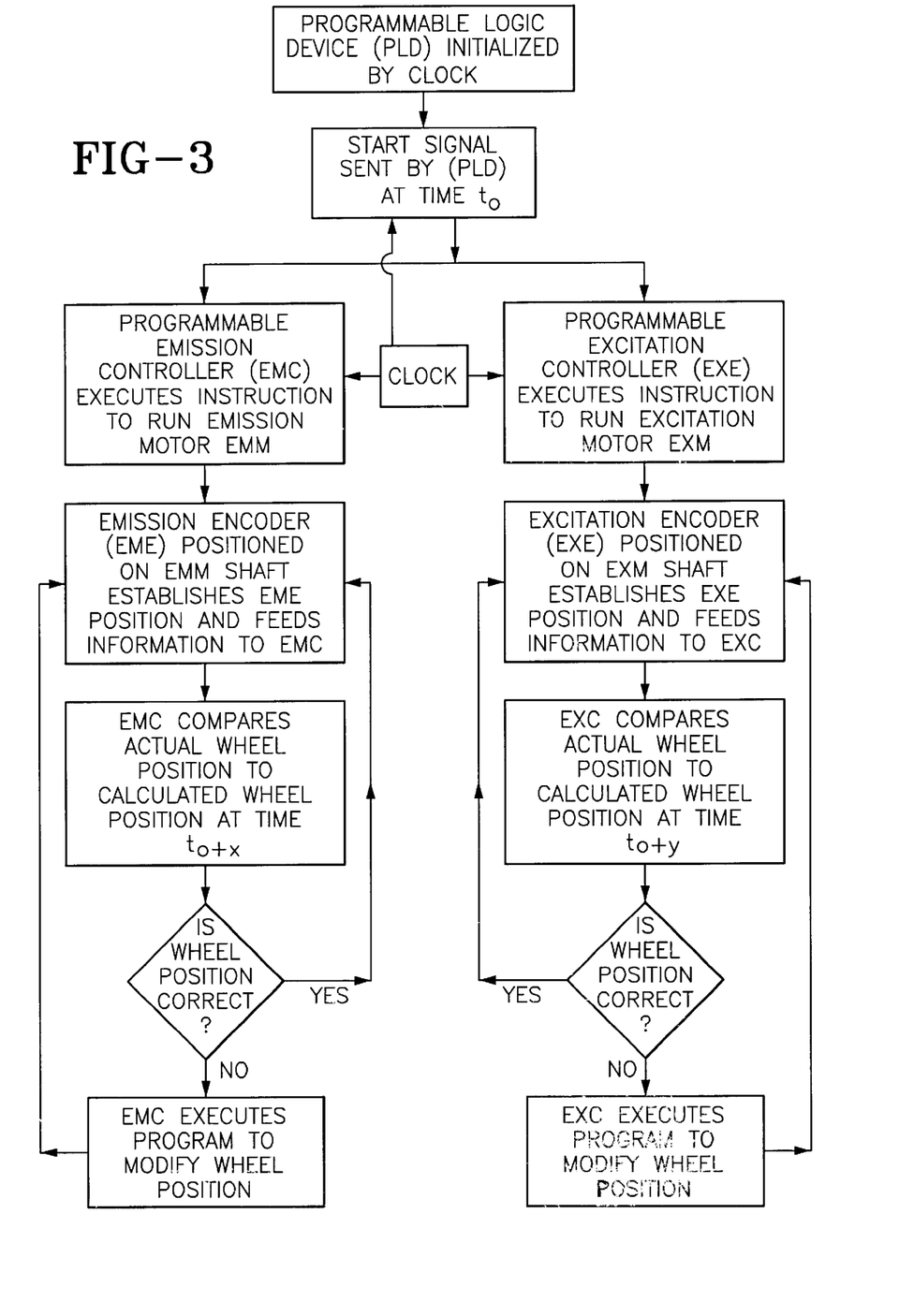
FIG. 3 is a flow diagram of the operation of the excitation and emission assemblies of the present invention in the fluorescent microscope applications of FIGS. 1 and 2.

Referring to FIGS. 2 and 3, a more detailed arrangement of the excitation assembly and the emission assembly of FIG. 1 is depicted. FIG. 2 is a schematic setting forth the arrangement that provides for the synchronization of the excitation and emission assembly, while FIG. 3 is a flow chart setting forth the information exchange among the components. Main CPU 280 processes one of a number of programs or subroutines, each program or subroutine providing a series of instructions that provide a mode of operation for the optical detecting and imaging device of the present invention. The operator preselects the mode of operation desired and the CPU sends a signal that initiates execution of a program for the selected mode of operation that is stored in programmable logic device (PLD) 270. This set of instructions is contained in the PLD because of economic concerns. Inexpensive CPUs that can run the program quickly enough allow for proper operation of the optical detecting and imaging device, while also servicing other tasks performed by the operating system are not currently available. Currently, however, it is necessary to use a set of instructions stored in a dedicated device, the PLD. With advances in the microcircuitry art, as faster CPU's become available at affordable prices, it is envisioned that the set of instructions could be run directly from the CPU. However, the best mode for operation of the present invention currently requires a dedicated preprogrammed hardware device such as PLD 270.

In addition to receiving information from CPU 280, PLD also receives signals and instructions, in a preferred embodiment, from excitation assembly 100, emission assembly 200 and clock 300 that are necessary for the execution of a preselected program. The excitation assembly 100 and emission assembly 200 are virtually identical in the preferred embodiment, except for preselected filters 112, 212 that are inserted into filter positions on filter wheels 110, 210, which may be of the same wavelength or of varying wavelengths. But the filter wheels may be varied so that the excitation and emission filter wheels contain different numbers of filter 112, 212 and different sizes of filters 112, 212. In fact, the only limitation on the number of the filters in either wheel is the ability to manufacture filter elements of the appropriate size and the ability to properly synchronize the operation of very small filter elements in either or both the excitation and emission assembly.

Each assembly 100, 200 includes a programmable motor controller 124, 224 that provides instructions in the form of signals to a motor driver 118, 218. Motor driver receives power from a power source 122, 222, which in the best mode of practicing the invention is a 12-volt power source, but which may readily be any source of power. In a preferred embodiment, only one power source is used to power both motor drivers. Motor driver 118, 218 in turn drives motor 114, 214. In the best mode of practicing the invention, the motor can rotate at a top speed of about 7500 rpm (125 revolutions per second), but may operate at a lower speed. It is understood that motors having higher speeds may be used, but in the preferred embodiment, the motor is capable of 7500 rpm and is satisfactory. Motors 114, 214 each have a motor shaft 116, 216. Attached to each shaft 116, 216 are an encoder 120, 220 and a filter wheel 110, 210 having a plurality of filter positions 112, 212 into which filters of preselected wavelength are assembled.

Figure 4:
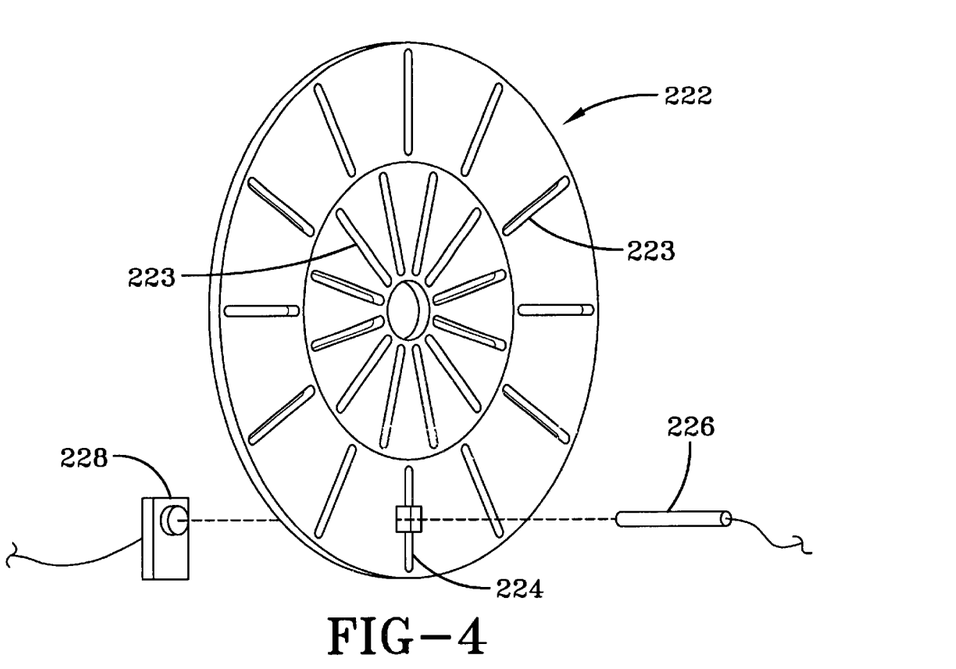
FIG. 4 is a perspective view of an encoder used in the preferred embodiment of the present invention.
Figure 5:
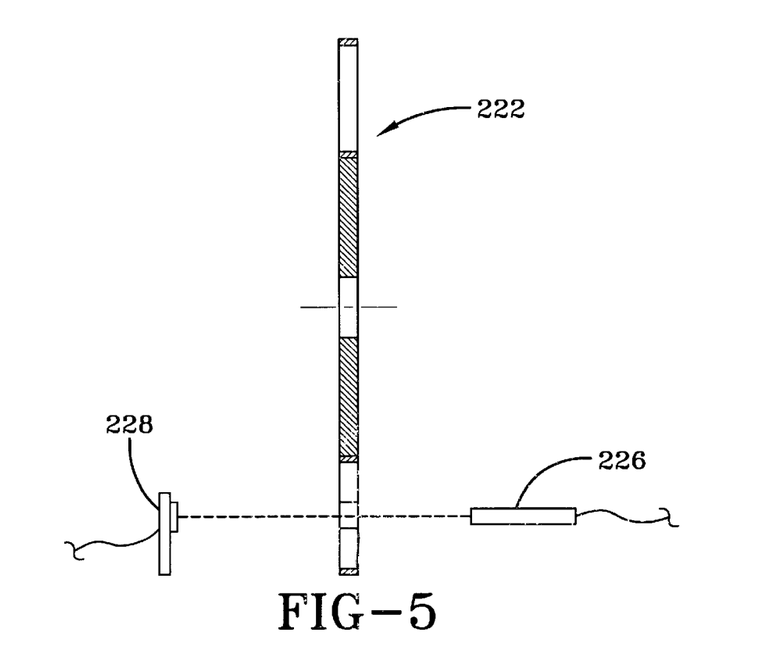
FIG. 5 is a side view of the encoder of FIG. 4.

In the preferred embodiment, encoder 120, 220 is an optical encoder. However, the encoder may also operate on magnetic or electrical principles, as long as it is capable of adequately resolving the position of the encoder as it rotates. Referring now to FIGS. 4 and 5, in a preferred embodiment, each optical encoder is a slotted wheel 222. It may include one ring having a plurality of slots. However, in the preferred embodiment, the encoder is a disk having two concentric rings, each ring having a plurality of slots 223, for example 512 slots. In addition to the concentric slotted rings, each encoder also includes a unique indexing slot 224 that produces an indexing pulse with each revolution of the encoder. A light emitting diode 226 is located on one side of the encoder, producing collimated light directed at the slotted rings. On the opposite side of the wheel is at least one integrated circuit detector 228 that includes at least one photocell and circuitry necessary to produce digital waveforms. As the encoder rotates, the light beam is interrupted by the slots in each of the rings. The integrated circuit detector detects these interruptions and generates the digital waveform resulting in a phasing relationship. Because the profiles are 90 degrees out of phase, the two resulting channels are in quadrature and the two slotted rings enable each encoder wheel to resolve 2048 discrete positions. Because the indexing slot 224 produces its own unique indexing pulse with each revolution of the optical encoder, the exact location of each of the discrete positions can be related to the position of the indexing pulse. In the best mode of practicing the invention, the encoder is a Hewlett Packard Model HEDS-5140, option I capable of 512 counts per revolution. However, the invention is not restricted to this encoder. Due to its high-resolution capability, the position of the optical encoder at any instant of time can be resolved to within about 0.17 degrees. For observations requiring less resolution, encoders having less capability may be used.

Since the filter wheel and the encoder are coupled to the same motor shaft, the filter wheel can also be resolved to the same degree of accuracy as the encoder, about 0.17 degrees in the preferred embodiment. Since the motor has a top regulated speed of 7500 rpm, or 125 revolutions per second, the encoder permits resolution of the filter wheel position theoretically within a time of about $4\times10^{-6}$ seconds. It is this ability to rapidly resolve the position of each filter wheel that permits synchronization of the excitation and emission filters wheels so that rapid observations of ongoing reactions can occur in biological samples. For example, once synchronized, the apparatus of the present invention permits 1000 observations or measurements per second in the preferred embodiment operating at top speed. This can be 1000 observations of a single wavelength or 125 measurements of each of eight different wavelengths every second. Clearly, the number of observations can be increased by increasing the number of filters in the filter wheel or by increasing the speed of the motor, so long as the limitations of the encoder to resolve the position of the filter wheel within 0.17 degrees is not exceeded. However, the invention will work satisfactorily at slower speeds and can detect emissions from a sample even when the encoder can resolve the position of the filter wheel at times as slow as $1\times10^{-3}$ seconds.

Referring again to FIGS. 2 and 3, in operation, PLD 270 and controllers 124, 224 are synchronized with one another by clock 300. To initiate operation, PLD 270 first sends a signal to each controller to index, that is, to return encoders to a position $P_0$. Optionally, controller may send a signal back to PLD 270 indicating that indexing is complete, but this is not required. After indexing, PLD 270 to sends a signal at time to $t_0$ both controllers 124, 224 to begin operation of a preselected program as instructed by the CPU 280. These signals are received by each of the programmable excitation controller 124 and programmable emission controller 224 in a simultaneous fashion. These controllers execute programs to begin operation of the respective motors 114, 214 by sending signals to respective motor drivers 118, 218 to initiate rotation of motor shafts 116, 216 respectively. The encoders 120, 220 transmit information in the form of signals, as previously described, to the controller to enable the controller to establish the filter wheel position to within the resolution capability of the encoders, 0.17 degrees in the preferred embodiment, and to use this information indicative of position for further computations. The controllers 124, 224 then compare the actual position of the encoder wheels as determined by the controller at a time $t_1$ with a calculated position of where the encoders are expected to be at time $t_1$. If the actual positions and calculated positions are not the same, then the respective controller 124, 224 sends a signal to the respective motor driver 118, 218 to change the speed of motor 114, 214. The process is constantly repeated, such as by execution of a continuous loop, to maintain the actual and calculated positions of each filter wheel 110, 210 as identical. Since the time to measure and to calculate the positions of each of the filter wheels and encoders and to make the required adjustments occurs in a very short time frame, controlled by clock frequency, the filter wheels remain in synchrony. In the best mode of practicing the invention, the clock operates at a is frequency of 1.8 Megahertz (MHz). Any speed faster than the speed of the clock in the preferred embodiment may be used as long as the controller is compatible with the faster clock speed. In the best mode of practicing of the invention, the controller is compatible with clock speeds up to 2 MHz. To assure that the adjustments will occur quickly so that they will not interfere observations of the experiment, it is desirable for the clock frequency that drives the operation of measurement and calculation of encoder position should drive the operation at least as fast as the encoder can resolve its position. This minimizes any lag that can otherwise occur. In the preferred embodiment set forth above, the encoder can resolve position in a theoretical time of about $4 \times 10^{-6}$ seconds, while the clock can drive the operation in a theoretical time of about $5 \times 10^{-7}$ seconds.

Controllers, synchronized by the clock and operating the same preselected programs, can operate independently while still performing the required operations to permit the required measurements or observations. As will be recognized by those skilled in the art, although the preferred embodiment utilizes two filter wheels each having eight filter positions moving in synchronization at the same speed, it will be apparent that synchronization can also be achieved by moving one wheel in a multiple with respect to the other wheel. For example, synchronization may be achieved by rotating the emission filter at eight times the speed of the excitation wheel, so that each of the emission filters will have an opportunity to detect light emitted from the sample as a result of one excitation wavelength. Similarly, one wheel may move at twice the speed of the other wheel to achieve yet different results. While a large number of combinations are possible, each can be achieved by making modifications to the software controlling the PLD and the associated controllers. It should also be apparent to those skilled in the art that this invention can be used to synchronize three or more filter wheels by the expansion of the principles set forth herein.

Although the present invention has been described in connection with specific examples and embodiments, those skilled in the art will recognize that the present invention is capable of other variations and modifications within its scope. These examples and embodiments are intended as typical of, rather than in any way limiting on, the scope of the present invention as presented in the appended claims.

What is claimed is:

1. A multichannel system for synchronizing independently driven filter wheels, comprising:

a means for controlling operation of the system by providing instructions;

a clock that provides timing signals;

a device with a programmable memory having the ability to receive and transmit signals, the device in communications with the clock and with the means for controlling operation of the system, the device receiving an instruction from the means for controlling operation of the system to execute a first preselected program and to transmit a signal in response to the instruction received from the means for controlling operation of the system;

at least two programmable motor controllers in communication with the clock to receive the timing signals, each being capable of being programmed to receive instructions from the device to run a second preselected program at a preselected time, the time determined by the timing signals from the clock;

at least two motor drivers, each motor driver connected to one of the at least two programmable motor controllers, each motor driver operating in response to an electrical signal from the controller;

a power source to provide power to the motor drivers;

a motor connected to each motor driver, each motor having a shaft;

an encoder rotatably mounted on each motor shaft, each encoder producing a plurality of pulses, and a means for indexing the position of the encoder on the motor shaft, the pulses being sent to the respective controller so that the respective controller can resolve the position of the encoder with respect to the indexing means; and a filter disk rotatably mounted to each motor shaft having a plurality of filter positions, and having a fixed position in relation to the encoder mounted on the motor shaft, the position of each encoder being synchronized by the timing signal from the clock so that the plurality of filter positions on each filter disk are synchronized with respect to one another.

2. A system for synchronizing a pair of independently driven filter wheels, comprising:

a central processing unit that controls operation of the system;

a clock that provides timing signals;

a programmable logic device with a programmable memory having the ability to receive and transmit signals, the logic device in communication with the clock and with the central processing unit, the logic device receiving an instruction from the central processing unit to execute a first preselected program and transmitting a signal in response to the instruction received from the central processing unit;

a first assembly comprised of a first programmable motor controller, a first motor driver, a first motor, a first encoder and a first filter wheel, the first programmable motor controller in communication with the clock to receive the timing signals and capable of being programmed to receive instructions from the logic device to run a second preselected program at a preselected time, the time determined by the timing signals from the clock, the first motor driver connected to the first programmable motor controller and operating in response to an electrical signal from the first motor controller, the first motor having a shaft and connected to the first motor driver, the first encoder rotatably mounted on the shaft of the first motor, the first encoder being further comprised of a disk having a plurality of slots, a light source positioned on the first side of the disk producing a beam of light incident on the disk as the disk is rotated on the shaft, a detector positioned on a second side of the disk that detects pulses of light transmitted through the slots of the rotating disk and digitizes the pulses, and a means for indexing the position of the first encoder on the shaft of the first motor, the digitized pulses being sent to the first controller so that the first controller can resolve the position of the first encoder with respect to the indexing means and the first filter wheel rotatably mounted to the shaft of the first motor and having a plurality of filter positions, the first filter wheel having a fixed position in relation to the first encoder on the shaft of the first motor, the position of the first encoder being determined by the shaft rotational speed, the timing signal from the clock and the position of the encoder with respect to the indexing pulse, so that one of the plurality of filters on the first filter disk can be positioned in a preselected position at a preselected time;

a second assembly comprised of a second programmable motor controller, a second motor driver, a second motor, a second encoder and a second filter wheel, the second programmable motor controller in communication with the clock to receive the timing signals and capable of being programmed to receive instructions from the logic device to run a second preselected program at a preselected time, the time determined by the timing signals from the clock, the second motor driver connected to the second programmable motor controller and operating in response to an electrical signal from the second motor controller, the second motor having a shaft and connected to the second motor driver, the second encoder rotatably mounted on the shaft of the second motor, the second encoder being further comprised of a disk having a plurality of slots, a light source positioned on a first side of the disk producing a beam of light incident on the disk as the disk is rotated on the shaft, a detector positioned on a second side of the disk that detects pulses of light transmitted through the slots of the rotating disk and digitizes the pulses, and a means for producing an indexing pulse for determining the initial position and subsequent positions of the second encoder on the shaft of the second motor, the digitized pulses being sent to the second controller so that the second controller can resolve the position of the second encoder with respect to the indexing means, and the second filter wheel rotatably mounted to the shaft of the second motor and having a plurality of filter positions, the second filter wheel having a fixed position in relation to the second encoder on the shaft of the second motor, the position of the second encoder being determined by the shaft rotational speed, the timing signal from the clock and the position of the second encoder with respect to the indexing pulse, so that one of the plurality of filters on the second filter disk can be positioned in a preselected position at the preselected time corresponding to the preselected position of the one of the filters on the first filter disk at the preselected time; and a power source to provide power to the motor drivers.

3. The system of claim 2 wherein the clock operates at a speed of at least about 100 kilohertz.

4. The system of claim 3 wherein the clock operates at a speed of about 1.8 megahertz.

5. The system of claim 2 wherein the first encoder disk and the second encoder disk each include a ring having a plurality of radial slots.

6. The system of claim 5 wherein the first encoder disk and the second encoder disk are further comprised of a pair of concentric rings, a first ring having a smaller diameter than a second ring, each ring having a plurality of radial slots, the radial slots of the first ring not being co-radial with the slots of the second ring.

7. The system of claim 6 wherein each ring of each encoder has 512 radial slots.

8. The system of claim 2 wherein the first filter wheel includes 8 filter positions and 8 filters.

9. The system of claim 2 wherein the second filter wheel includes 8 filter positions and 8 filters.

10. The system of claim 8 wherein each of the filters produces a single wavelength of light different than the wavelengths of the other filters.

11. The system of claim 9 wherein each of the filters produces a single wavelength of light different than the wavelengths of the other filters.

12. A fluorometer for observing activity of a reaction occurring in a sample, comprising:

a central processing unit to control the operations of the microscope;

a clock that provides timing signals;

a programmable logic device the receives instructions from the central processing unit and timing signals from the clock, and that provides instructions;

a light source that produces a broadband beam of light;

an infrared filter to remove, by filtering, light from the infrared spectrum;

a first focusing lens to focus the filtered light;

an excitation assembly upon which the filtered light is focused, the excitation assembly comprised of a first programmable motor controller, a first motor driver, a first motor, a first encoder and a first filter wheel, the first programmable motor controller in communication with the clock to receive the timing signals and programmed to receive instructions from the programmable logic device to run a second preselected program at a preselected time, the time determined by the timing signals from the clock, the first motor driver connected to the first programmable motor controller and operating in response to an electrical signal from the first motor controller, the first motor having a shaft and connected to the first motor driver, the first encoder rotatably mounted on the shaft of the first motor, the first encoder being further comprised of a disk having a plurality of slots, a light source positioned on the first side of the disk producing a beam of light incident on the disk as the disk is rotated on the shaft, a detector positioned on a second side of the disk that detects pulses of light transmitted through the slots of the rotating disk and digitizes the pulses, and a means for indexing the position of the first encoder on the shaft of the first motor, the digitized pulses being sent to the first controller so that the first controller can resolve the position of the first encoder with respect to the indexing means and the first filter wheel rotatably mounted to the shaft of the first motor and having a plurality of filter positions, the first filter wheel having a fixed position in relation to the first encoder on the shaft of the first motor, the position of the first encoder being determined by the shaft rotational speed, the timing signal from the clock and the position of the encoder with respect to the indexing pulse, causing a preselected one of the plurality of filters on the first filter disk to be positioned in a preselected position at a preselected time so that infrared-filtered light from the focusing lens is filtered by the one preselected filter at the preselected time to produce light of a single wavelength;

a first light guide to receive, guide and transmit the light of the single wavelength from the filter;

a collimating lens to receive the light transmitted from the light guide and collimate the light;

a sample chamber that receives the single wavelength light, directs the single wavelength of light onto the sample, thereby exciting the sample that acts as a second source of light as it is emits light as it decays;

a second focusing lens to focus the light emitted by the sample;

a second light guide to receive, guide and transmit the light emitted from the sample;

an emission assembly to receive light from the light guide emitted by the sample, the emission assembly comprised of a second programmable motor controller, a second motor driver, a second motor, a second encoder and a second filter wheel, the second programmable motor controller in communication with the clock to receive the timing signals and capable of being programmed to receive instructions from the logic device to run a second preselected program at a preselected time, the time determined by the timing signals from the clock, the second motor driver connected to the second programmable motor controller and operating in response to an electrical signal from the second motor controller, the second motor having a shaft and connected to the second motor driver, the second encoder rotatably mounted on the shaft of the second motor, the second encoder being further comprised of a disk having a plurality of slots, a light source positioned on a first side of the disk producing a beam of light incident on the disk as the disk is rotated on the shaft, a detector positioned on a second side of the disk that detects pulses of light transmitted through the slots of the rotating disk and digitizes the pulses, and a means for producing an indexing pulse for determining the initial position and subsequent positions of the second encoder on the shaft of the second motor, the digitized pulses being sent to the second controller so that the second controller can resolve the position of the second encoder with respect to the indexing means, and the second filter wheel rotatably mounted to the shaft of the second motor and having a plurality of filter positions, the second filter wheel having a fixed position in relation to the second encoder on the shaft of the second motor, the position of the second encoder being determined by the shaft rotational speed, the timing signal from the clock and the position of the second encoder with respect to the indexing pulse, so that one of the plurality of filters on the second filter disk can be positioned in a preselected position at the preselected time corresponding to the preselected position of the one of the filters on the first filter disk at the preselected time causing a preselected one of the plurality of filters on the second filter disk to be positioned in a preselected position at the preselected time so that light emitted by the sample is filtered by the preselected one filter at the preselected time to produce a second light of a single wavelength;

a third focusing lens to focus the second single wavelength of light from the emission assembly; and means for observing the light from the third focusing lens.

13. The fluorometer of claim 12 wherein the means for observing includes an optical objective.

14. The fluorometer of claim 12 further including a photomultiplier tube to amplify the second single wavelength of light from the third focusing lens and convert the light to a signal.

15. The fluorometer of claim 14 wherein the means for observing includes a storage device to store the signal from the photomultiplier tube for later observation.

16. The fluorometer of claim 12 wherein the means for observing the light includes a CCD camera for observing the light and a display for visual display of the signal from the camera.

17. The fluorometer of claim 16 further including means for storing the signal received by the display from the camera.

18. The fluorometer of claim 12 wherein the sample chamber is a fluorescent microscope that additionally includes a dichroic mirror and an objective, the dichroic mirror directing the received single wavelength of light through an objective onto the sample.

19. A method for synchronizing at least a first and a second independently operated filter wheel assembly, each assembly including an associated motor and motor controller, used in conjunction with a light source to excite a sample and a detector to observe rapidly occurring activity in the sample, comprising the steps of:

placing the sample in an observation chamber;

providing a signal from a central control unit to move the first filter wheel assembly and the second filter wheel assembly to preselected initial positions;

providing light from a light source;

providing a signal from the control unit to the motor controllers to load a preselected program into a memory of the motor controller; then providing a signal from the control unit to the motor controllers to simultaneously execute the preselected program, thereby moving the filter wheel assemblies by activating the motors to predetermined locations at predetermined times;

transmitting light of a predetermined wavelength through one of a plurality of filters on the first filter wheel assembly onto the sample, thereby exciting the sample;

detecting light emitted by the sample;

directing the detected emitted light from the sample onto the second filter wheel assembly to filter light from the sample;

observing light having a wavelength characteristic of a reaction on-going in the sample transmitted through one of a plurality of filters on the second filter wheel assembly at a preselected time.

20. A method for observing a sample in fluorometer using at least a first and a second independently operated filter wheel assembly, each assembly being synchronized in operation with the other and including an associated motor and motor controller, used in conjunction with a light source to excite a samples and a detector to observe rapidly occurring activity in the sample, comprising the steps of:

placing the sample in an observation chamber;

providing a signal from a central control unit to move the filter wheel assemblies to preselected initial positions;

providing light from a light source;

providing a signal from the control unit to the motor controllers to load a preselected program into a memory of the motor controller; then providing a signal from the control unit to the motor controllers to simultaneously execute the preselected program, thereby moving the filter wheel assemblies by activating the motors to predetermined locations at predetermined times;

transmitting light of a predetermined wavelength through one of a plurality of filters on the first filter wheel assembly onto the sample, thereby exciting the sample;

detecting light emitted by the sample;

directing the detected emitted light from the sample onto the second filter wheel assembly to filter light from the sample;

observing light having a wavelength characteristic of a reaction on-going in the sample transmitted through one of a plurality of filters on the second filter wheel at a preselected time.

21. The method of claim 20 wherein the step of placing the sample in an observation chamber includes placing the sample in a fluorescent microscope.

* * * * *